United States Patent
Cronimus

(10) Patent No.: US 6,642,724 B2
(45) Date of Patent: Nov. 4, 2003

(54) VALVE SEATING WITH ELECTRODES, ESPECIALLY FOR <<ENAMEL-TEST>> TYPE CONTROL DEVICE

(75) Inventor: Georges Cronimus, Gumbrechtshoffen (FR)

(73) Assignee: DE Dietrich Process Systems, Zinswiller (FR)

( * ) Notice: Subject to any disclaimer, the term of this patent is extended or adjusted under 35 U.S.C. 154(b) by 0 days.

(21) Appl. No.: 09/910,692

(22) Filed: Jul. 20, 2001

(65) Prior Publication Data

US 2002/0011581 A1 Jan. 31, 2002

(30) Foreign Application Priority Data

Jul. 28, 2000 (FR) .............................. 00 09974

(51) Int. Cl.[7] .............................................. G01R 27/08
(52) U.S. Cl. ...................................... 324/718; 324/515
(58) Field of Search ................................ 324/557, 425, 324/510, 694, 515, 718; 340/605; 251/129.01

(56) References Cited

U.S. PATENT DOCUMENTS

| | | |
|---|---|---|
| 3,555,414 A | 1/1971 | Deichelmann |
| 3,789,297 A * | 1/1974 | Frolich .................. 324/694 |
| 3,858,114 A | 12/1974 | Voellmin et al. |
| 5,912,561 A * | 6/1999 | Mack .................. 324/718 |

FOREIGN PATENT DOCUMENTS

| | | |
|---|---|---|
| EP | 0 501 817 | 9/1992 |
| EP | 0 773 359 | 5/1997 |
| GB | 2 072 853 | 10/1981 |

OTHER PUBLICATIONS

De Dietrich: Auto–adaptive EmailTest AZ (no date available).*
Montoring of the Glass–Lining: the EmailTest AZ (no date available).*

* cited by examiner

*Primary Examiner*—Jay Patidar
*Assistant Examiner*—Walter Benson
(74) *Attorney, Agent, or Firm*—Davis & Bujold, P.L.L.C.

(57) ABSTRACT

A valve seating (23) is made from a fluoridated polymer, for example, solid glass-coated PTFE or reinforced PFA. At least one electrode (24) is attached to or integral with the valve seating and made of conductive material, such as graphite-TEFLON®, that is compatible with the valve seating. The valve seating is especially for use in conjunction with a device for verifying the integrity of an enamel coating of the "enamel-test" type. The valve seating is then used on the waste valve (11) of the container to be checked and two electrodes (24) are disposed so as to be in contact with the contents (8).

15 Claims, 5 Drawing Sheets

VALVE SEATING WITH ELECTRODES, ESPECIALLY FOR <<ENAMEL-TEST>> TYPE CONTROL DEVICE

FIELD OF THE INVENTION

The present invention concerns a seating for a valve, a flow control outlet, or the like, comprising electrodes, specifically for use in detecting flaws in a layer of enamel, currently known as an "enamel-test".

BACKGROUND OF THE INVENTION

The seating according to the invention is preferably intended for the waste valve of a reactor, a tank, a column, or other container having an interior coating of enamel which must be tested for defects.

In the chemical industry it is sometimes necessary to utilize or store reagents or products that are particularly acidic or corrosive, making it impossible to use reactors, tanks, columns or other conventional containers with steel walls that would be attacked and deteriorate.

One solution in these cases is to use reactors or other containers with interior walls that are coated with a protective layer of enamel. This highly resistant, inert coating ensures that the reactor or container will be protected from corrosion by the contents.

However, to eliminate both the risk of container deterioration and the risk of leaks potentially dangerous to humans, equipment and the environment, the integrity of this protective coating must be assured at all times.

There must be a permanent means of controlling the condition of enamel layer. To do this, manufacturers use devices which detect flaws in the enamel layer, currently called "enamel-tests".

To detect any possible enamel flaws, such a device must have three electrodes, one of which is connected to the metal mass of the container to be checked and the two others in contact with the liquid inside the container.

The two electrodes in contact with the liquid measure a reference current between them, which allows the conductivity of the liquid inside the reactor to be checked. To verify the continuity of the enamel layer, this device is used to measure the intensity of the current existing between the unit of these two electrodes and the metal mass of the reactor, using the third electrode. If there is a flaw in the enamel, a current leak is detected, which is proportionate in intensity to the area of the non-enameled surface.

Such a device allows simple, continuous verification of the integrity of the enamel layer. Possible flaws can be detected very early, thus preventing them from becoming worse or causing dangerous leaks, and making repairs easy and inexpensive.

To verify the integrity of the enamel coating, the two electrodes in contact with the liquid must be positioned as low as possible in the container to be controlled. For this reason, they are generally placed near the waste valve, which is obviously at the lowest point on the container.

According to the prior art, these electrodes are integral with the upper surface of the block on the piston of the waste valve, with the piston being movable between an upper position and a lower position, respectively corresponding to the open and closed valve positions. The wire conductors connecting these electrodes to the "enamel-test". apparatus pass through the piston rod in the usual way.

Since the piston of the waste valve is in permanent contact with the corrosive environment inside the container, it must also be coated with protective enamel. Specific conductive materials must be used for this enamel layer, with a dilatation coefficient compatible with that of the enamel and similar chemical resistance, when constructing electrodes to be integrated within the upper surface of the piston head.

These electrodes are generally made of platinum or iridium when platinum is not sufficiently resistant to the corrosive action of the reactive environment. Therefore, these electrodes are rather expensive due to the use of these materials and their complex construction.

Moreover, if there is a problem with these electrodes or in the piston enamel, which is the reactor portion most frequently exposed to various forces (abrasion, mechanical shock, etc.), then it becomes necessary to change the entire blocking piston. Since this piston is completely enameled, it is quite expensive.

SUMMARY OF THE INVENTION

The object of the invention is to propose a device with integrated electrodes that is less expensive, easily replaceable, and which can be used in an enamel-coated container equipped with an "enamel-test" device.

To resolve this technical problem, the invention proposes a valve seating comprising at least one electrode and preferably two, which may either be attached to or integrated within said seating. These electrodes may be used, for example, inside a device that controls the integrity of an enamel coating such as an "enamel-test" device, but they are not limited to such a use.

The valve seating according to the invention is made using a fluoridated polymer, such as a TEFLON®-coated material, preferably solid glass-coated TEFLON® or reinforced TEFLON®. This makes it resistant to the aggressive environment and because it is flattened, it forms a tight seal when the piston stop, in the lowered position, contacts it.

Each of the electrodes is made of conductive material compatible with the material of the valve seating so that it can either be attached to the body of the valve seating or integrated within it. Thus, it is preferably, but not necessarily, made of graphite TEFLON®. The cost of such an electrode, perfectly adapted to the most corrosive environments, is considerably lower than a platinum or iridium electrode inserted into the piston enamel.

Furthermore, if there is a problem requiring electrode replacement, the valve seating of the invention can be quickly and easily dismounted and reattached by removing and replacing the valve without having to remove the piston from it. Since it is not enameled but made from a fluoridated polymer, the valve seating of the invention is economical, certainly much less expensive than an enameled piston.

The valve seating according to the invention may be used in conjunction with a device for regulating the condition of an enamel coating of the "enamel-test" type, although it is not limited to this use.

The seating of the invention is placed on the waste valve of the container to be checked in the lowest possible position for complete regulation. It comprises two electrodes, preferably in the form of conductive contact studs extending from the upper wall of the seating so as to contact the container.

BRIEF DESCRIPTION OF THE DRAWINGS

Other characteristics and features of the invention will be obvious from reading the following detailed description with reference to the attached drawings, in which.

DESCRIPTION OF PREFERRED EMBODIMENTS

Figure 1:
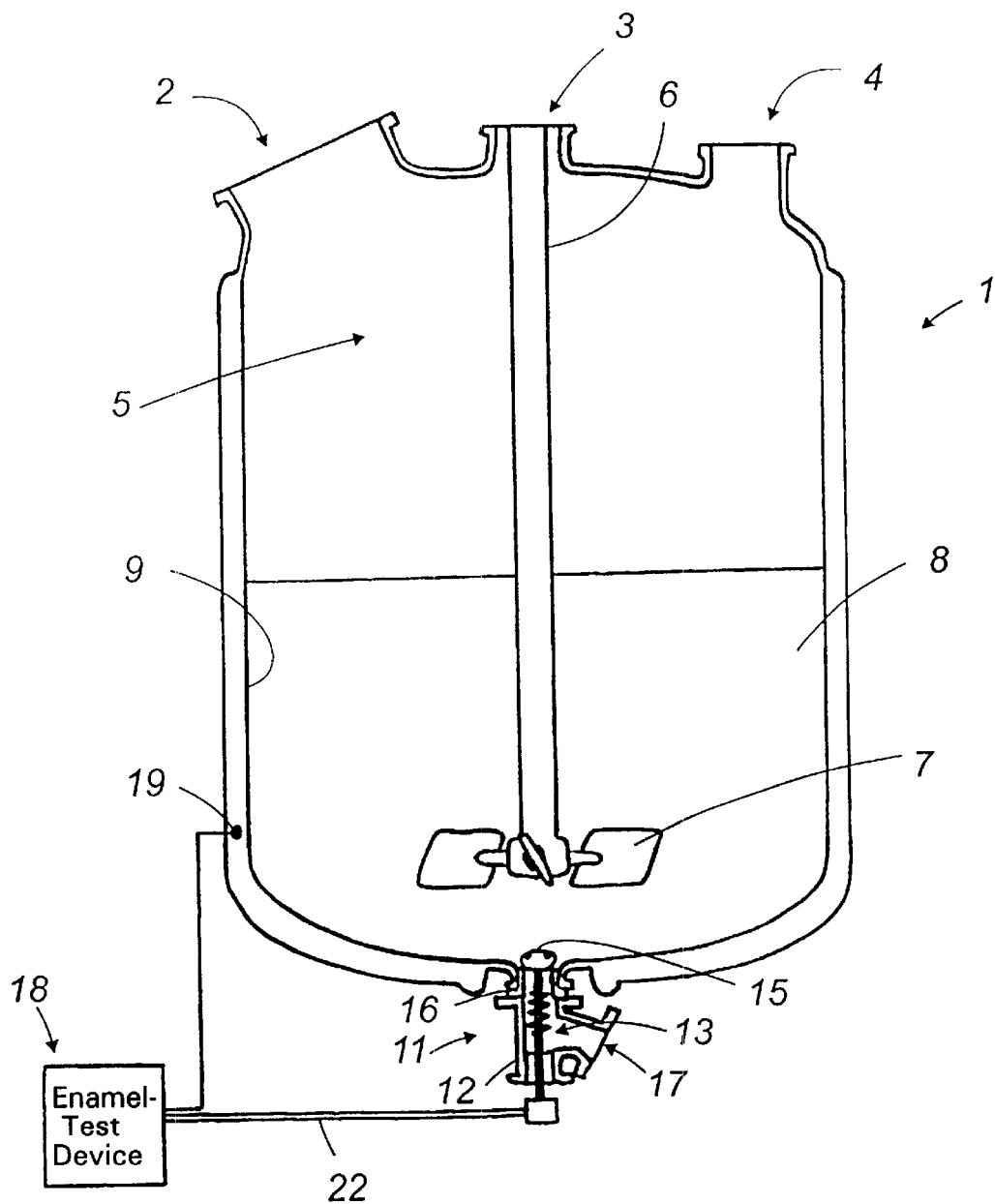
FIG. 1 is a schematic longitudinal cross-section of an enameled chemical reactor with a conventional "enamel-test" device installed comprising electrodes disposed according to the prior art, located in the block of the movable piston of the waste valve.

The valve seating with integrated electrodes according to the present invention will now be described in detail with reference to FIGS. 1 through 8. Equivalent elements in the different drawings will bear the same reference numerals.

The first two drawings show a reactor equipped with a device for regulating a layer of enamel currently known as "enamel-test" comprising electrodes located inside the piston of the waste valve, as in the prior art.

FIG. 1 shows a chemical reactor 1 with three upper openings 2, 3 and 4 which can be used to introduce the different reactants, solvents and catalysts or to plunge various instruments or accessories (agitator, mole, probe, gripping means) into reactor 1.

Reactor 1 is equipped with a mechanical agitator 5 with a shaft 6 which passes through central opening 3 and extends down toward the lower portion of the reactor. Shaft 6 terminates in a unit of three angled blades 7 which stir the contents, liquid, solution or reactive environment 8 in reactor 1 when the shaft is rotated by a drive motor, not shown, located outside the reactor.

To make it resistant to the highly corrosive reactive environment 8, the interior surface of reactor 1 may be completely coated with a protective enameled layer 9. In the same way, all the surfaces that may come into contact with reactive environment 8 should also be enamel-coated. Obviously, this is true for shaft 6 and blades 7 on agitator 5.

In the conventional way, reactor 1 has at its lowest point an orifice 10 with a waste valve 11 for completely emptying the contents.

Waste valve 11 comprises a stationary valve body 12 and a piston 13 that moves within the valve body between an upper position and a lower position for opening and closing waste valve 11, respectively. Piston 13 comprises a shaft 14 and a block 15 which is also coated with enamel.

When in the lower closed position, shown in FIGS. 1 through 4, block 15 contacts the upper portion 16 of a valve seating interposed between reactor orifice 10 and body 12 of waste valve 11, thereby forming a tight seal for waste valve 11 of reactor 1.

When in the upper open position, not shown, block 15 of movable piston 13 is upwardly displaced, freeing a path for reactive environment 8 inside reactor 1 to flow out through seating 16 and then body 12 of the valve until it reaches an evacuation opening 17.

Enameled reactor 1 is equipped with a device 18 for controlling the continuity of the protective enamel layer 9 currently known as an "enamel-test".

This "enamel-test" apparatus or device 18 comprises three electrodes, one electrode 19 being connected to the metal mass of container 1 and the two others 20 in contact with the reactive environment 8 contained inside the container.

In order to detect a flaw in any location in reactor 1, the two electrodes 20 must be positioned as low as possible within the reactor. According to the prior art illustrated in FIGS. 1 and 2, they are integral with the upper surface of the block 15 of piston 13 of waste valve 11.

Conductive wires 21 pass through shaft 14 of piston 13 to connect electrodes 20 to conductors 22 of the "enamel-test" device 18.

Block 15 of piston 13 is also coated with a protective enamel layer, since it is in permanent contact with reactive environment 8 inside the container. This enamel layer requires the use of specific conductive materials which are compatible with the enamel and capable of resisting the pressure it exerts in the construction of electrodes 20 integrated with the upper surface of the piston head.

These electrodes are generally made of platinum or iridium when platinum is not sufficiently resistant to reactive environment 8. Thus, electrodes 20 are quite expensive.

Furthermore, if there is a problem, piston 13 must be completely changed, and this is relatively expensive because it is enamel-coated.

Figure 4:
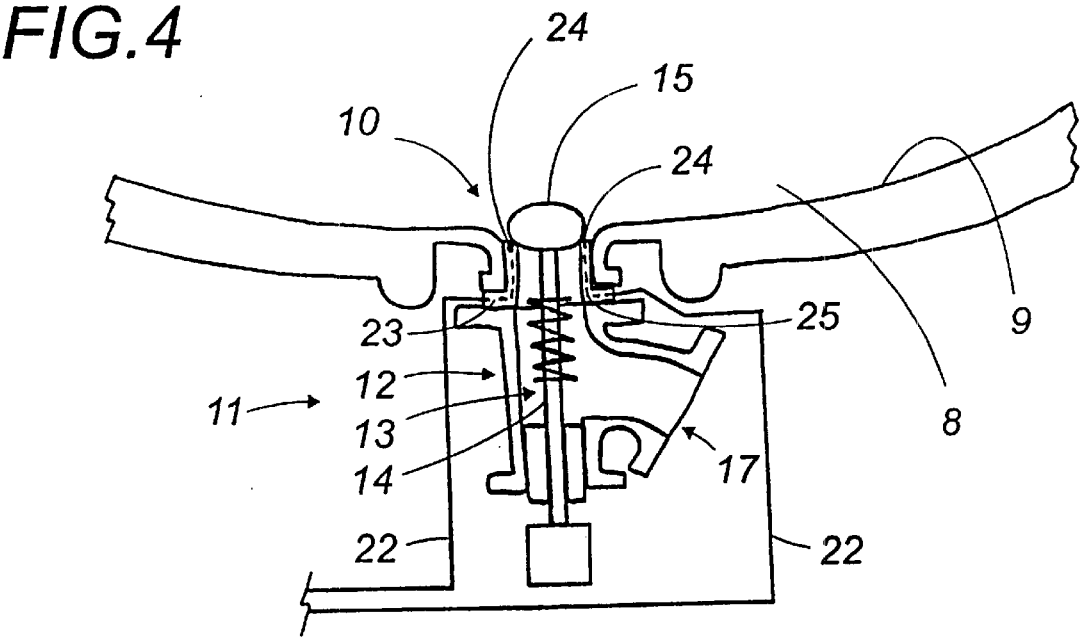
FIG. 4 is an enlarged cross-section of the lower portion of the reactor of FIG. 3, showing the waste valve with more particularity and its seating enclosing the electrodes of the enamel-test in accordance with the invention.
Figure 3:
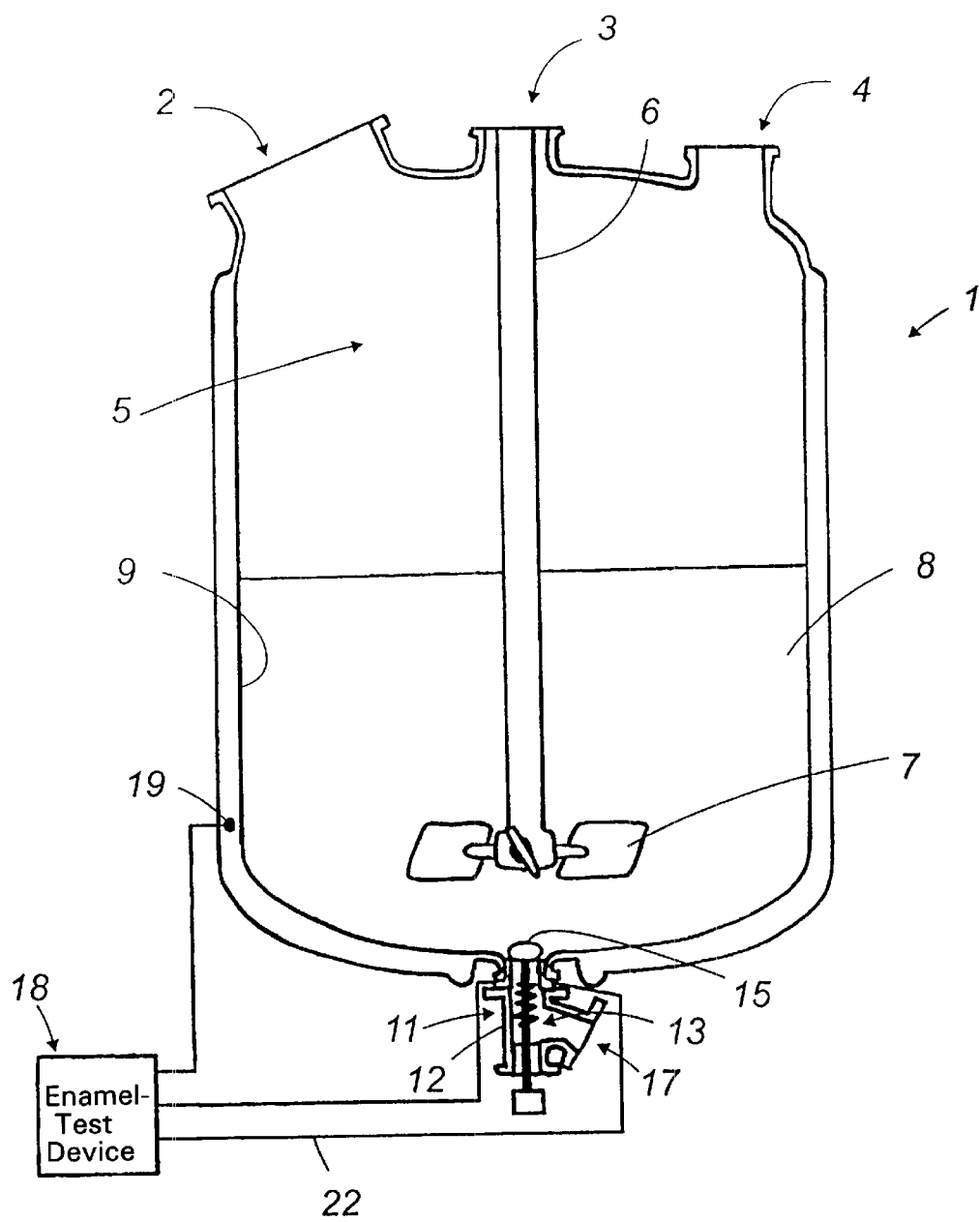
FIG. 3 is a schematic longitudinal cross-section of an enameled chemical reactor having a waste valve equipped with a seating according to the present invention comprising electrodes for an "enamel-test" device.

FIGS. 3 and 4 show a reactor 1 equipped with a valve seating comprising electrodes according to the present invention.

Figure 2:
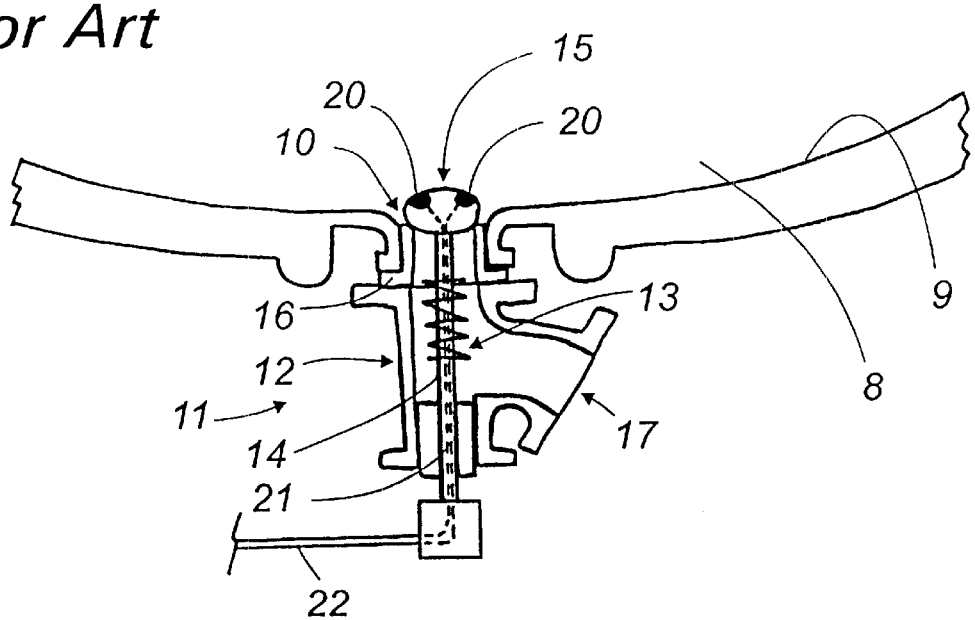
FIG. 2 is an enlarged cross-section of the lower portion of the reactor of FIG. 1, showing the waste valve with more particularity and its movable piston on which the "enamel-test" electrodes are located according to the prior art.

Reactor 1 is identical to that shown in FIGS. 1 and 2. It has the same openings 2, 3 and 4 in the upper portion and it is equipped with a mechanical agitator 5 with an essentially vertical shaft 6 terminating in three angled, blades 7. Its interior surface is covered with a layer of enamel 9 protecting it from the reactive environment 8.

At its lowest point, the reactor has an orifice 10 equipped with a waste valve 11 comprising, in the usual manner, a stationary valve body 12 and a piston movable within the valve body between a lower, closed position and an upper, open position where the contents can escape through evacuation orifice 17 in valve 12.

A valve seating 23 is interposed between enameled reactor orifice 10 and the stationary valve body 12.

When in the lower, closed position, shown in FIGS. 3 and 4, block 15 of piston 13 contacts the upper portion of the valve seating 23, thereby tightly sealing waste valve 11 of reactor 1.

Enameled reactor I is also equipped with an "enamel-test" device 18 for assuring the continuity of protective enamel layer 9. This device must be connected to three electrodes, one electrode 19 being in contact with the metal mass of reactor 1 and the two others in contact with reactive environment 8.

Valve seating 23 comprises, according to the invention, at least one electrode 24 either attached to or integral with it. In the various embodiments shown in FIGS. 3 through 7, the valve seating, according to the invention, has two electrodes. However, this is merely an illustrative example and is in no way limiting, since the number of electrodes in the seating can vary according to the anticipated use.

If it is to be used in conjunction with an "enamel-test" type device, valve seating 23 according to the invention preferably comprises two electrodes 24 located near its upper wall so as to contact reactive environment 8 inside the reactor to be regulated.

When valve seating 23, according to the invention, is positioned within reactor 1, its upper wall is located at the lowest point within reactor 1, which is especially advantageous. Electrodes 24 located in this area can thus detect any flaw in the enamel at any location in the reactor. It is even possible to control the enamel of block 15 on piston 13 located above.

Conductive wires 25 pass through valve seating 23 in order to connect electrodes 24 to exterior conductors 22 and thereby to "enamel-test" device 18.

Valve seating 23, according to the invention, will now be described in more detail with reference to FIGS. 5 through 7.

Valve seating 23 has a generally tubular body 26 defining a hollow interior space 27 which receives movable shaft 14 of piston 13 and allows fluid to pass through when valve 11 is in the open position.

The upper portion of the internal wall of cylindrical body 26 preferably has a chamfer with a conical surface 28 for improved contact between block 15 and valve seating 23 and forming a perfect seal on the valve when it is in the closed position.

Cylindrical body 26 extends at the lower portion into a peripheral flange 29 extending toward the exterior of the valve seating 23 and, for example, generally perpendicular to cylindrical body 26. When the, valve seating 23 is installed on reactor 1, it is held in position by clamping said flange 29 between the clamp of reactor orifice 10 and the clamp of the tubular inlet on the body of valve 12.

To form a complete seal, flange 29 preferably has two perimeter grooves 30 formed in its lateral wall for receiving two flat annular gaskets.

The size, shape, and angle of cylindrical body 26 and flange 29 may vary from what has been shown and described previously. These parameters are selected as a function of orifice 10 and valve 11 so that seating 23 can be adapted to them to the greatest extent possible.

According to the invention, valve seating 23 comprises at least one electrode 24 and preferably two, which are attached or affixed in some way. One or more conductors 25 connect these electrodes to some apparatus, for example, to "enamel-test" device 18.

Figure 5:
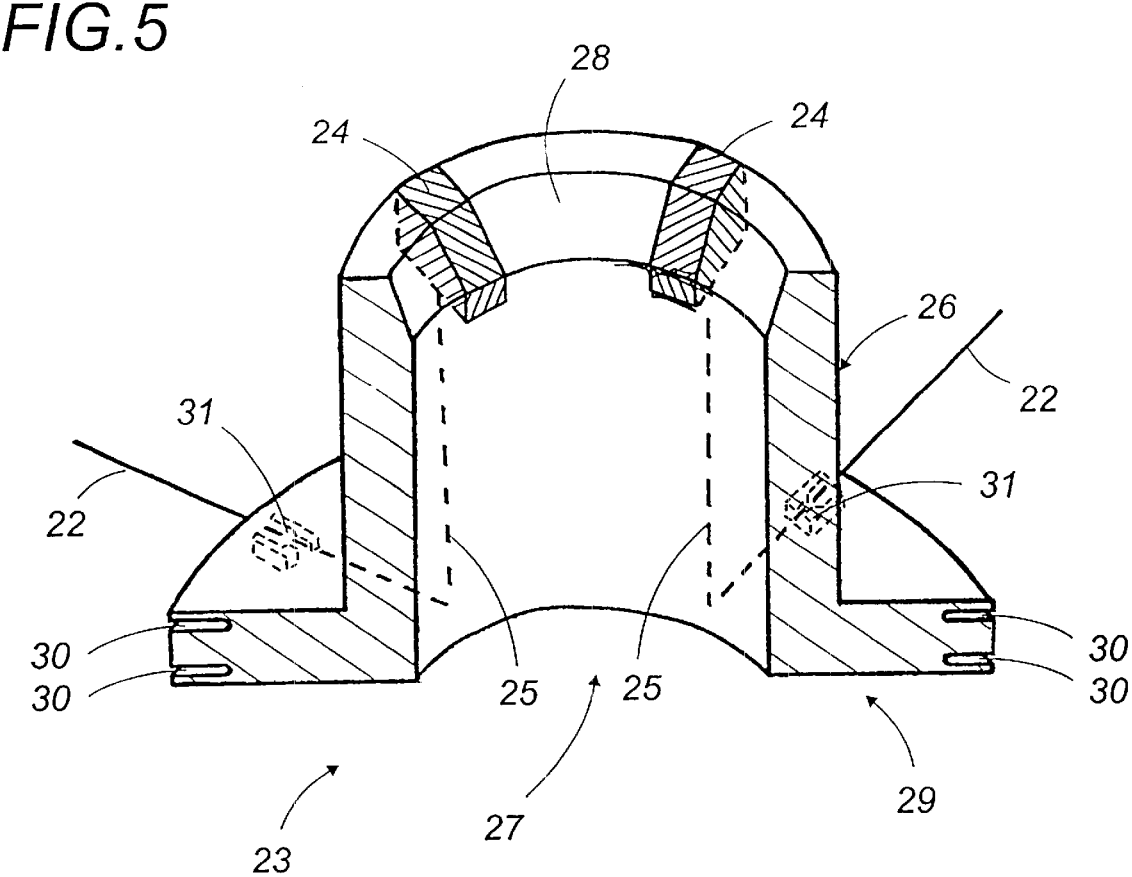
FIG. 5 is a cross-section in perspective of one embodiment of the valve seating according to the present invention comprising electrodes which may be Used for an "enamel-test"
Figure 6:
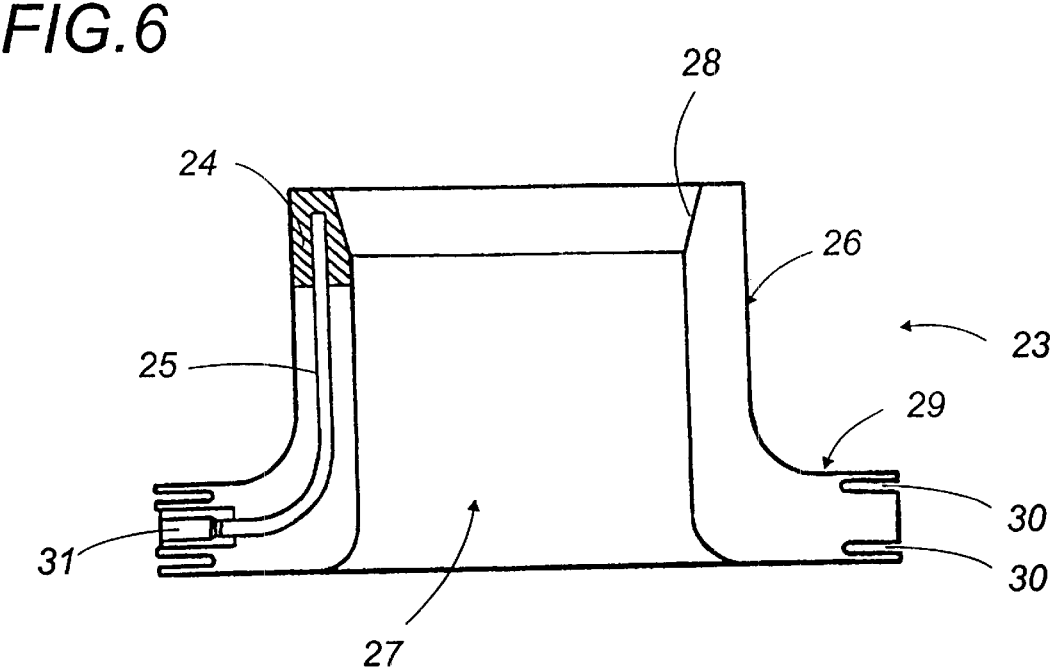
FIG. 6 is a longitudinal cross-section of another embodiment of the valve seating according to the present invention.
Figure 7:
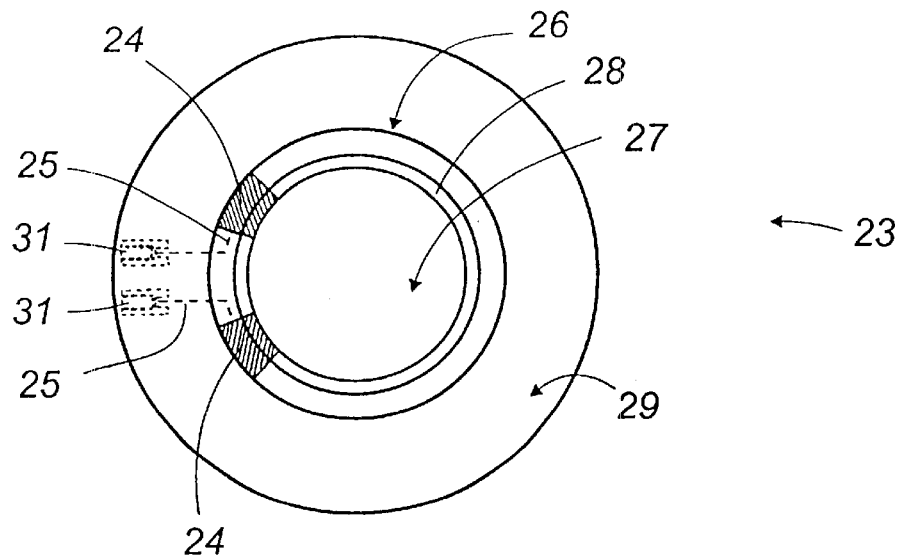
FIG. 7 is an overhead view showing the manner in which the valve seating of FIG. 6 is constructed.

According to a preferred embodiment, shown in FIGS. 5 through 7, valve seating 23 comprises two electrodes 24 that are integral with its upper wall. Said electrodes 24 preferably take the form of conductive contact-studs inserted during molding or incorporated into the material so they become an integral portion of valve seating 23. They emerge from the upper wall of the seating in order to come in contact with reactive environment 8.

In another variation, each electrode can consist of one specific zone of the valve seating material, with conductive inclusions or inserts.

Conductive wires 25 extending from electrodes 24 may, for example, pass through the wall of valve seating 23 and terminate at connectors 31 located near an accessible position in valve seating 23. Said connectors 31, preferably located in the lateral wall of flange 29, allow electrodes 24 to be connected to device 18 using exterior conductors 22 that may be connected to it.

According to a preferred embodiment, illustrated in FIG. 7, connectors 31 are advantageously regrouped in a single accessible area on valve seating 23, for example a single area on flange 29, thus forming a single connection zone.

The valve seating according to the invention is preferably made from a fluoridated polymer such as, for example, a Teflon®-coated material. This makes it resistant to corrosion from the environment and because it is flat, it forms a tight seal when block 15 of piston 13, in the lower position, contacts it. It might also be made of solid glass-coated PTFE or PFA reinforced with an internal steel skeleton.

Each of the electrodes 24 is thus made of a conductive material that is compatible with the material of valve seating 23, allowing it to be either attached to or integrated within the body of the valve seating. It is preferably, but not necessarily, made of graphite-Teflon®. Other materials could also be used, such as for example, graphite or precious metals.

Figure 8:
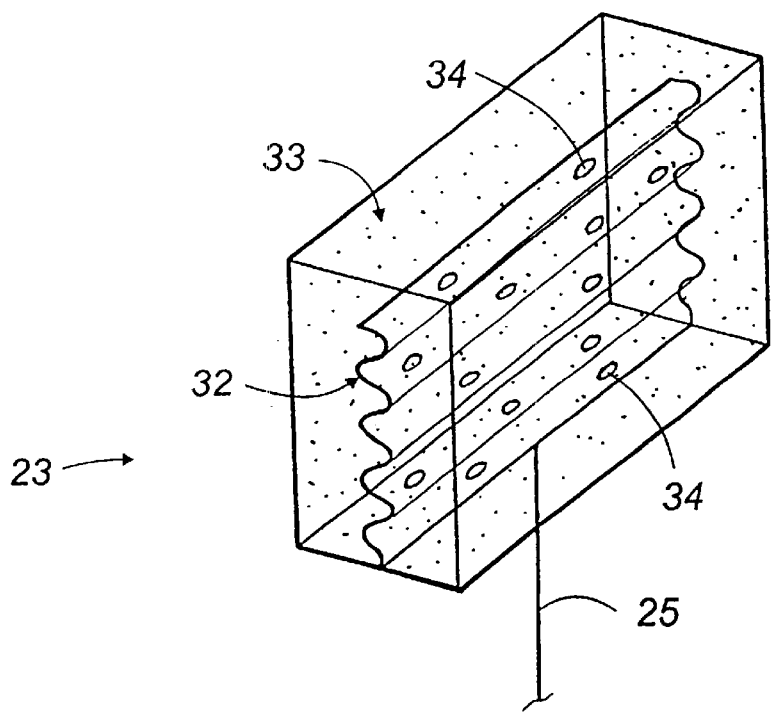
FIG. 8 is a perspective view of one manner of constructing an "enamel-test" electrode that can be integrated into the valve seating of the invention.

One non-limiting example, among others, of an electrode that can be integrated within valve seating 23, according to the invention, has been illustrated in FIG. 8.

Electrode 24 comprises a metal plate 32 connected to conductor 25 and incorporated into a block 33 of graphite-Teflon®. Plate 32 is preferably undulating and contains a plurality of perforations 34 so the graphite-Teflon® penetrates through plate 32 during the molding process, which improves its stability.

Block 33 in FIG. 8 is generally parallelepiped in shape, but it may be any other shape that is better suited to integration within the seating of valve 23. In particular, it may have a chamfered surface as in FIGS. 5 through 7.

The seating for a valve with electrodes according to the invention is particularly well adapted for use in conjunction with an "enamel-test" device. However, it should be understood that its use is, not limited to this application. It can also be used with any type of apparatus requiring electrodes, whether they are in contact with a reactive environment or not. For example, another possible application for the valve seating, according to the invention, is using the electrodes to detect when the reactor is empty.

Similarly, the valve seating of the invention is not limited to use with a waste valve in an enameled reactor. Such a seating could be useful with numerous types of valves on various types of containers, enameled or not, such as for example, reactors, tanks, columns, and the like.

What is claimed is:

1. A valve seating for a valve of a container having a conductive metal body and a protective layer on an inner surface of the container to protect the body of the container from contents of the container, the valve seating interacting with a valve piston to control flow of the contents through the valve, the valve seating being adapted for monitoring of a condition of the protective layer on the inner surface of the container by monitoring an electrical current through the protective layer and comprising:
  a generally tubular body for receiving the piston and having,
    an upper surface mating with the piston in a sealing relationship, and an exterior surface mating with a valve opening in the container in a sealing relationship, and at least a first electrode exposed to the contents of the container which is one of attached to and integral with the valve seating, at least the first electrode being of a conductive material compatible with the valve seating and connectable to an monitoring apparatus for monitoring the condition of the protective layer on the inner surface of the container.

2. The valve seating according to claim 1, wherein the valve seating is made of fluoridated polymer.

3. The valve seating according to claim 2, wherein the valve seating is made of solid glass-coated PTFE.

4. The valve seating according to claim 2, wherein the valve seating is made of reinforced PFA.

5. The valve seating according to claim 2, wherein the valve seating is designed to be placed on a waste valve of the container.

6. The valve seating according to claim 1, wherein the monitoring apparatus for monitoring the condition of the protective layer on the inner surface of the container is an enamel test apparatus and the valve seating includes the first and a second electrodes for operation with the enamel test apparatus.

7. The valve seating according to claim 6, wherein at least one of the first and second electrodes is positioned in order to be in contact with contents of the container.

8. The valve seating according to claim 6, wherein at least one of the first and second electrodes is in the form of a conductive contact-stud inserted during the molding process and forming as an integral part of the seat of the valve.

9. The valve seating according to claim 1, wherein at least one of the first and second electrodes is capable of being connected to at least one of a measurement apparatus and a detection apparatus by means of a conductor passing through the body of the valve seating.

10. The valve seating according to claim 1, wherein the valve seating comprises at least one connector located near an accessible area on the valve seating for connecting the at least one electrode to an apparatus by means of an exterior conductor to the apparatus.

11. The valve seating according to claim 10, wherein a plurality of connectors are grouped on a single accessible area on the valve seating to form a single connection zone.

12. The valve seating according to claim 1, wherein at least the first electrodes comprises a fluoridated polymer material.

13. The valve seating according to claim 1 wherein the conductive material of at least the first electrodes comprises a flouridated polymer material; and at least the first electrodes comprises a metal plate connected to a conductor and molded inside a block of the flouridated polymer material.

14. The valve seating according to claim 13, wherein the plate is undulating and perforated with a plurality of openings.

15. The valve seat of claim 1, wherein the protective layer is enamel and the monitoring apparatus is an enamel test apparatus.

* * * * *